US012752091B2

(12) United States Patent
Ahn

(10) Patent No.: US 12,752,091 B2
(45) Date of Patent: Oct. 6, 2026

(54) METHOD FOR MANUFACTURING FRACTIONAL MICRONEEDLE MODULE HAVING PARTITIONED ZONES HIGH FREQUENCY

(71) Applicant: AGNES MEDICAL CO., LTD, Seongnam-si (KR)

(72) Inventor: Gunyoung Ahn, Seongnam-si (KR)

(73) Assignee: AGNES MEDICAL CO., LTD, Seongnam-si (KR)

(*) Notice: Subject to any disclaimer, the term of this patent is extended or adjusted under 35 U.S.C. 154(b) by 762 days.

(21) Appl. No.: 18/031,911

(22) PCT Filed: Oct. 22, 2020

(86) PCT No.: PCT/KR2020/014462
§ 371 (c)(1),
(2) Date: Apr. 14, 2023

(87) PCT Pub. No.: WO2022/085815
PCT Pub. Date: Apr. 28, 2022

(65) Prior Publication Data

US 2023/0364415 A1 Nov. 16, 2023

(30) Foreign Application Priority Data

Oct. 19, 2020 (KR) ........................ 10-2020-0135251

(51) Int. Cl.
*A61M 37/00* (2006.01)
*A61N 1/40* (2006.01)
(Continued)

(52) U.S. Cl.
CPC ........... *A61M 37/0015* (2013.01); *A61N 1/40* (2013.01); *A61M 2037/0053* (2013.01);
(Continued)

(58) Field of Classification Search
CPC ...... A61M 2037/0053; A61M 37/0015; A61M 2037/0061; A61N 1/40; A61N 1/328;
(Continued)

(56) References Cited

U.S. PATENT DOCUMENTS

2019/0184366 A1* 6/2019 Henderson ........ A61M 37/0015

FOREIGN PATENT DOCUMENTS

JP 2010-502268 A 1/2010
JP 2015136528 A * 7/2015 ........ A61M 37/0015
(Continued)

OTHER PUBLICATIONS

Oku et al., "Development of a new type of fabrication process in microneedles", 2017 International Symposium on Micro-NanoMechatronics and Human Science (MHS), Nagoya, Japan, 2017, pp. 1-4, (Year: 2017).*

*Primary Examiner* — A. Dexter Tugbang
(74) *Attorney, Agent, or Firm* — Bridgeway IP Law Group, PLLC; Jihun Kim

(57) ABSTRACT

A method for manufacturing a fractional microneedle module includes generating a conductive flat plate and partitioning it into m×m parts to generate N partitioned zones. M grooves are formed within these partitioned zones, into which M fractional microneedles are inserted. Each needle is connected to an electrical connection terminal to receive a high-frequency signal. The method further involves distributing high-frequency energy to each of the N partitioned zones through the needles. In one embodiment, electrically isolated switching elements, such as photo field effect transistors (FETs), are connected to the partitioned zones to control current flow. The microneedles may further include an insulating film made of parylene or Teflon coated on the needle body.

11 Claims, 5 Drawing Sheets

(51) Int. Cl.

| | |
|---|---|
| *A61N 1/05* | (2006.01) |
| *A61N 1/06* | (2006.01) |
| *A61N 1/32* | (2006.01) |
| *A61N 1/36* | (2006.01) |

(52) U.S. Cl.
CPC .... *A61M 2037/0061* (2013.01); *A61N 1/0502* (2013.01); *A61N 1/06* (2013.01); *A61N 1/328* (2013.01); *A61N 1/36017* (2013.01); *Y10T 29/49222* (2015.01)

(58) Field of Classification Search
CPC .... A61N 1/36017; A61N 1/0502; A61N 1/06; Y10T 29/49222
See application file for complete search history.

(56) References Cited

FOREIGN PATENT DOCUMENTS

| | | | |
|---|---|---|---|
| KR | 10-2014-0086275 | A | 7/2014 |
| KR | 10-2016-0038566 | A | 4/2016 |
| KR | 20180141580 | A | 11/2018 |
| KR | 10-2019-0088953 | A | 7/2019 |
| KR | 10-2117711 | B1 | 6/2020 |

* cited by examiner

| | |
|---|---|
| ▶ Sp1 | 70.3℃ |
| ▶ Sp2 | 71.3℃ |
| ▶ Sp3 | 70.9℃ |
| ▶ Sp4 | 18.2℃ |

METHOD FOR MANUFACTURING FRACTIONAL MICRONEEDLE MODULE HAVING PARTITIONED ZONES HIGH FREQUENCY

TECHNICAL FIELD

The present invention relates to a method for manufacturing a fractional microneedle module having partitioned zones using high frequency, and more particularly, to a method for manufacturing a fractional microneedle module having partitioned zones using high frequency, capable of uniformly distributing high-frequency energy to a portion of the skin and a local site to be treated by partitioning a fractional microneedle patch and applying a high-frequency signal to needles in the partitioned zones.

BACKGROUND ART

Fractional micro-needling technology used in the related art is a fractional high-frequency (radio frequency (RF)) treatment using the physical treatment of microneedles and RF high-frequency energy, and is a treatment that induces scarring and pore relief through collagen regeneration by inserting fractional microneedles into a site in contact with the skin to reduce stimulation on the skin surface and instantaneous discharge high-frequency heat energy to the dermal layer.

Generally, microneedles are used to deliver active substances such as drugs and vaccines in vivo and to detect an analyte in the body and to perform a biopsy. Accordingly, recently, the microneedle is being applied to a treatment device that activates cell tissue by applying high frequency to the microneedle and directly delivering high-frequency energy to the dermal layer of the skin through the microneedle to maintain elastic skin and minimize skin aging. That is, the microneedle is used as a device in which when high-frequency (RF) energy is applied to the human body, the energy is converted into thermal energy in the human body, and the thermal energy raises the temperature inside the human body to obtain a medical treatment or cosmetic effect.

As an example of the microneedle treatment method, Korean Patent Laid-Open Publication No. 2018-0141580 (May 26, 2020) discloses a skin treatment needle configured to increase the speed of skin regeneration by supplying energy into skin tissue, and including a needle body that is formed of a conductive material and inserted into the skin from a front end thereof, wherein the needle body has an outer circumferential surface in which a partial region includes a conductive portion, which is a region inducing an electric field different from those formed at other portions of the needle body, and the conductive portion includes a plurality of creases to cause the electric field formed through the conductive portion to have a uniform distribution without being concentrated in one place, and a skin treatment device.

However, in the case of the fractional microneedle patch of the related art, the high-frequency energy distribution is concentrated only at an edge of the patch into which the needles are inserted, and the energy distribution decreases toward the center portion. That is, there is a problem that the energy distribution is non-uniformly formed and thus the site to be treated is not treated well.

DISCLOSURE

Technical Problem

The present invention is directed to providing a method for manufacturing a fractional microneedle module having partitioned zones using high frequency, capable of minimizing the damage to the epidermal layer caused by a microneedle to which the high frequency is applied, and uniformly distributing energy to each partitioned zone of a patch according to the purpose of treatment so that a portion of the skin and a local site are effectively treated.

Technical Solution

One aspect of the present invention provides a method for manufacturing a fractional microneedle module having partitioned zones using high frequency, the method including generating a flat plate made of a conductive material, partitioning the flat plate having conductivity into m×m parts to generate N partitioned zones, generating M grooves into which fractional microneedles are inserted in the N partitioned zones and inserting M fractional microneedles into the grooves, connecting each of the M needles with an electrical connection terminal so that a high-frequency signal is applied thereto, and uniformly distributing high-frequency energy to each of the N partitioned zones so that the energy is uniformly injected into a dermal layer of the skin due to the M needles electrically connected to the electrical connection terminal.

According to an embodiment of the present invention, the method may further include lowering the degree of skin damage and increasing safety by distributing energy of 1/N of input power to each of the N partitioned zones when the high-frequency (radio frequency (RF)) signal is applied to the fractional microneedles.

According to an embodiment of the present invention, the method may include arranging an interval between the needles at a boundary between one zone of the N partitioned zones, in which the energy of 1/N of the input power is distributed, and a zone adjacent to the one zone, such that a generated electric field of each zone is not affected.

According to an embodiment of the present invention, the method may include providing an insulating film coated with an insulating material on a remaining portion of an outer circumferential surface of a body of each of the fractional microneedles except for a conductive portion, and providing the insulating film as a parylene or Teflon material.

Another aspect of the present invention provides a method for manufacturing a fractional microneedle module having partitioned zones and using radio frequency, the method comprising generating a flat plate made of a conductive material, partitioning the flat plate having conductivity into m×m parts to generate N partitioned zones, generating M grooves into which fractional microneedles are inserted in the N partitioned zones and inserting M fractional microneedles into the grooves, connecting electrically isolated switching elements serving as switches in parallel for each of the N partitioned zones so that current is conducted sequentially or non-sequentially between the N partitioned zones, allowing a high-frequency signal to be applied to each of the M needles connected to an electrical connection terminal as the electrically isolated switching element is turned on, and injecting the high-frequency signal with an energy intensity of 1/N of input power to each of the N partitioned zones due to the M needles being electrically connected to the electrical connection terminal.

According to an embodiment of the present invention, the electrically isolated switching element may serve as an on/off switch, and only perform a role of turning on or off by inputting light (photo) as a signal to a gate (G) of the element.

According to an embodiment of the present invention, the method may include connecting X field effect transistor (FET) elements in parallel to form the electrically isolated switching element and allowing the switching element to serve as one switch, and distributing in parallel an amount of power input to the electrically isolated switching element due to the configuration of connecting the X FET elements in parallel.

According to an embodiment of the present invention, the method may further include controlling the switches in adjacent zones to switch in the same pattern to prevent a phenomenon of instantaneous high voltage from appearing due to ripple noise (high-frequency noise) generated at a boundary between one zone of the N partitioned zones and a zone adjacent to the one zone when the electrically isolated switching element is switched from off to on.

According to an embodiment of the present invention, the method may further include applying the input power only to a portion of the N partitioned zones to which the high-frequency signal is input by allowing the same input signal to be transmitted to a gate of each of the N electrically isolated switching elements and non-sequentially switching each of the N electrically isolated switching elements to be turned on or off.

According to an embodiment of the present invention, the method may further include sequentially applying the input power to the N partitioned zones by allowing the same input signal to be transmitted to a gate of each of the N electrically isolated switching elements and sequentially switching each of the N electrically isolated switching elements to be turned on or off.

According to an embodiment of the present invention, the method may further include providing a switch control module allowing the same input signal to be transmitted to a gate of each of the N electrically isolated switching elements and configured to control the electrically isolated switching elements to be sequentially or non-sequentially switched.

Advantageous Effects

In a method for manufacturing a fractional microneedle module having partitioned zones using high frequency according to the present invention, damage to the epidermal layer caused by a microneedle to which the high frequency is applied can be minimized, energy can be uniformly distributed to each partitioned zone of a patch according to the purpose of treatment so that a certain portion of the skin and a local site can be effectively treated, and safety can be increased since the degree of skin damage is reduced due to the uniform energy distribution.

MODES OF THE INVENTION

Figure 1:
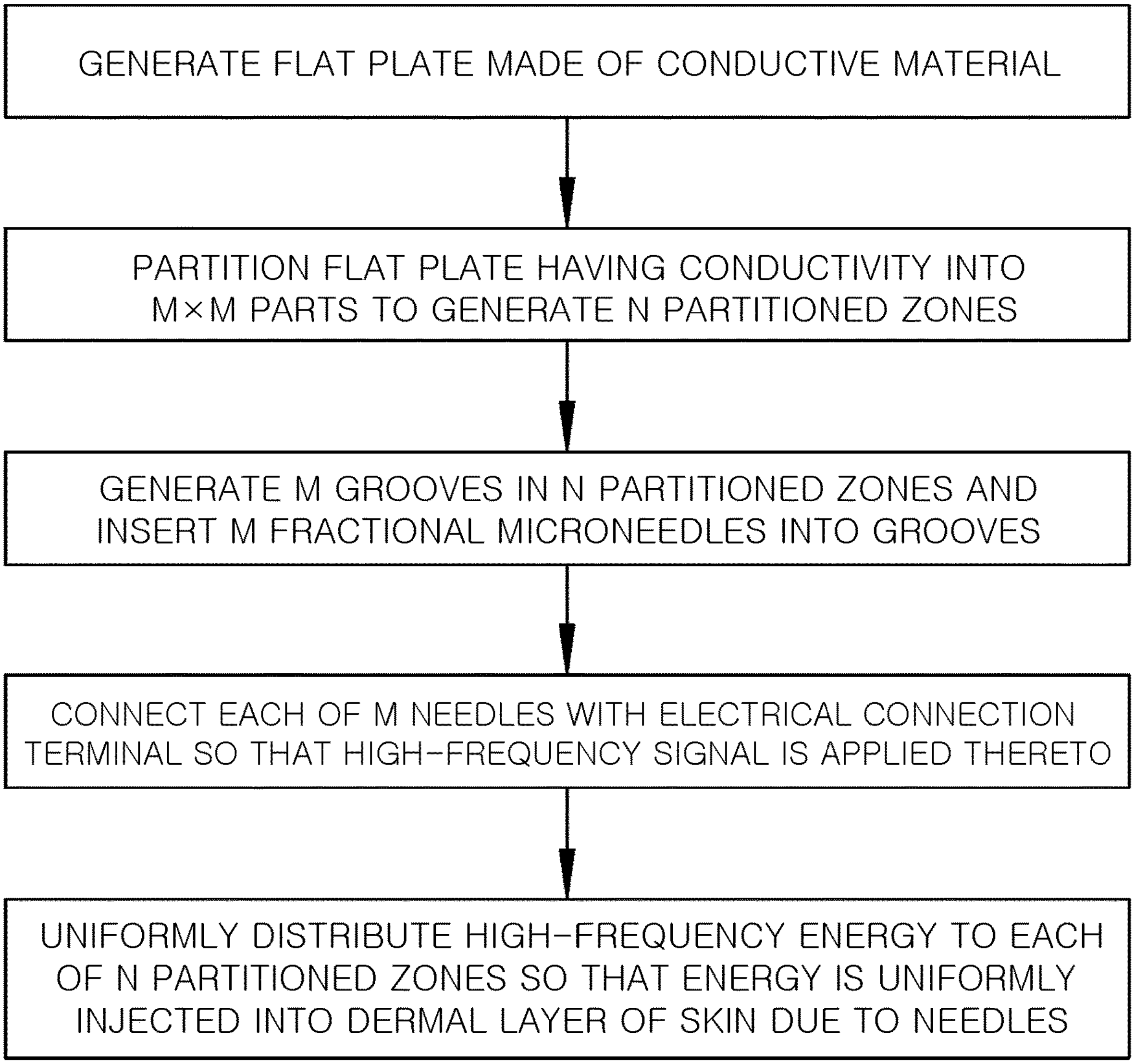
FIG. 1 is a flowchart of a zone partitioning method according to one embodiment of the present invention.

A method for manufacturing a fractional microneedle module having partitioned zones using high frequency according to embodiments of the present invention will be described in detail with reference to the accompanying drawings. While the present invention is susceptible to various modifications and alternative forms, specific embodiments thereof are shown by way of example in the drawings and will herein be described in detail in the text. However, the description is not intended to limit the present invention to the specific embodiments, and it should be understood that the present invention is to cover all modifications, equivalents, and alternatives that fall within the spirit and scope of the present invention. In describing each drawing, like reference numerals represent like components. In the accompanying drawings, dimensions of structures are shown larger than actual dimensions for clarity of the present invention or smaller than actual dimensions in order to understand a schematic configuration.

In addition, while terms such as "first," "second," and the like may be used to describe various components, such components should not be limited by the above terms. These terms are only used to distinguish one component from another. For example, without departing from the scope of the present invention, a first component may be referred to as a second component, and similarly, a second component may be referred to as a first component. Meanwhile, unless otherwise defined, all terms used herein including technical or scientific terms have the same meanings as those generally understood by one of ordinary skill in the art. It should be further understood that terms, such as those defined in commonly used dictionaries, should be interpreted as having a meaning that is consistent with their meaning in the context of the relevant art and are not to be interpreted in an idealized or overly formal sense unless expressly so defined herein.

FIG. 1 is a flowchart of a zone partitioning method according to one embodiment of the present invention.

Referring to FIG. 1, a method for manufacturing a fractional microneedle module having partitioned zones using high frequency includes generating a flat plate made of a conductive material, partitioning the conductive flat plate into m×m parts to generate N partitioned zones, generating M grooves into which fractional microneedles can be inserted in the N partitioned zones and inserting M fractional microneedles into the grooves, connecting each of the M needles with an electrical connection terminal so that a high-frequency signal can be applied thereto, and uniformly distributing high-frequency energy to each of the N partitioned zones so that the energy is uniformly injected into the dermal layer of the skin due to the M needles being electrically connected to the electrical connection terminal.

The method further includes lowering the degree of skin damage and increasing safety by distributing energy of 1/N of input power to each of the N partitioned zones by partitioning the conductive flat plate into m×m parts and applying a high-frequency (radio frequency (RF)) signal to the fractional microneedles in the N partitioned zones. The method further includes arranging an interval between the needles at the boundary between one zone of the N partitioned zones, in which the energy of 1/N of the input power is distributed, and the zone adjacent to the one zone, such that a generated electric field of each zone is not affected. Here, the method includes providing an insulating film coated with an insulating material on a remaining portion of an outer circumferential surface of a body of each of the fractional microneedles except for a conductive portion, and providing the insulating film as a parylene or Teflon material.

Figure 2:
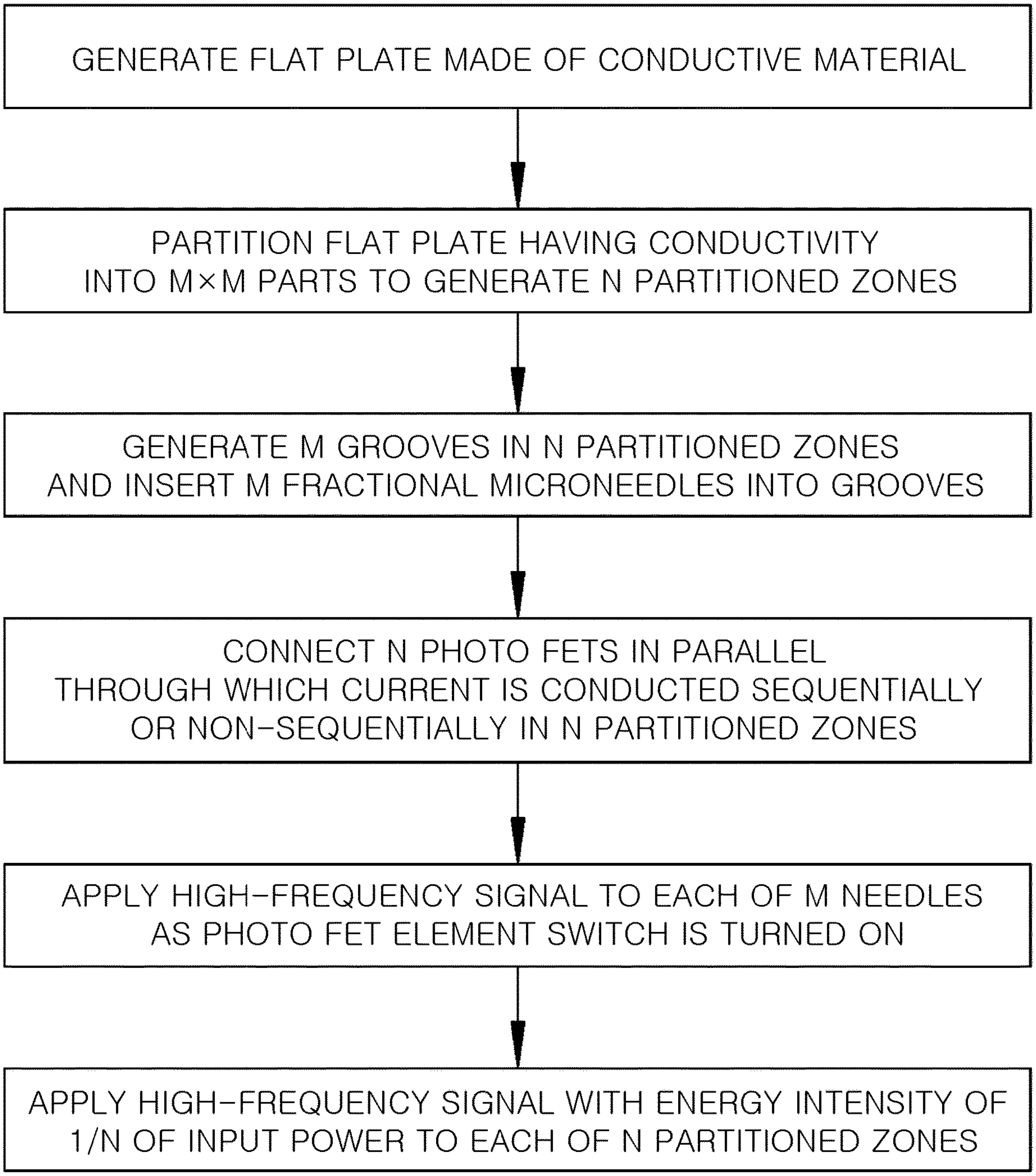
FIG. 2 is a flowchart of a method for applying a high-frequency signal with an energy intensity of 1/N of power to each of N partitioned zones according to one embodiment of the present invention.

FIG. 2 is a flowchart of a method for applying a high-frequency signal with an energy intensity of 1/N of power to each of N partitioned zones according to one embodiment of the present invention.

Referring to FIG. 2, the present invention includes generating a flat plate made of a conductive material, partitioning the flat plate having conductivity into m×m parts to generate N partitioned zones, generating M grooves into which fractional microneedles can be inserted in the N partitioned zones and inserting M fractional microneedles into the grooves, connecting electrically isolated switching elements serving as switches in parallel for each of the N partitioned zones so that current can be conducted sequentially or non-sequentially between the N partitioned zones, allowing a high-frequency signal to be applied to each of the M needles connected to an electrical connection terminal as the electrically isolated switching element is turned on, and injecting the high-frequency signal with an energy intensity of 1/N of input power to each of the N partitioned zones due to the M needles being electrically connected to the electrical connection terminal.

Here, each of the electrically isolated switching elements serves as an on/off switch, and may only perform a role of turning on or off by inputting light (photo) as a signal to a gate G of the element. In addition, the method includes connecting X field effect transistor (FET) elements in parallel to form the electrically isolated switching element and allowing the switching element to serve as one switch, and distributing in parallel an amount of power input to the electrically isolated switching element due to the configuration of connecting the X FET elements in parallel. In addition, the method further includes controlling the switches in adjacent zones to switch in the same pattern to prevent the phenomenon of instantaneous high voltage from appearing due to ripple noise (high-frequency noise) generated at the boundary between one zone of the N partitioned zones and the zone adjacent to the one zone when the electrically isolated switching element is switched from off to on, and applying input power only to a portion of the N partitioned zones to which the high-frequency signal is input by allowing the same input signal to be transmitted to a gate of each of the N electrically isolated switching elements and non-sequentially switching each of the N electrically isolated switching elements to be turned on or off. In addition, the method further includes sequentially applying input power to the N partitioned zones by allowing the same input signal to be transmitted to a gate of each of the N electrically isolated switching elements and sequentially switching each of the N electrically isolated switching elements to be turned on or off. The method further includes providing a switch control module allowing the same input signal to be transmitted to a gate of each of the N electrically isolated switching elements and capable of controlling the electrically isolated switching elements to be sequentially or non-sequentially switched.

Figure 3:
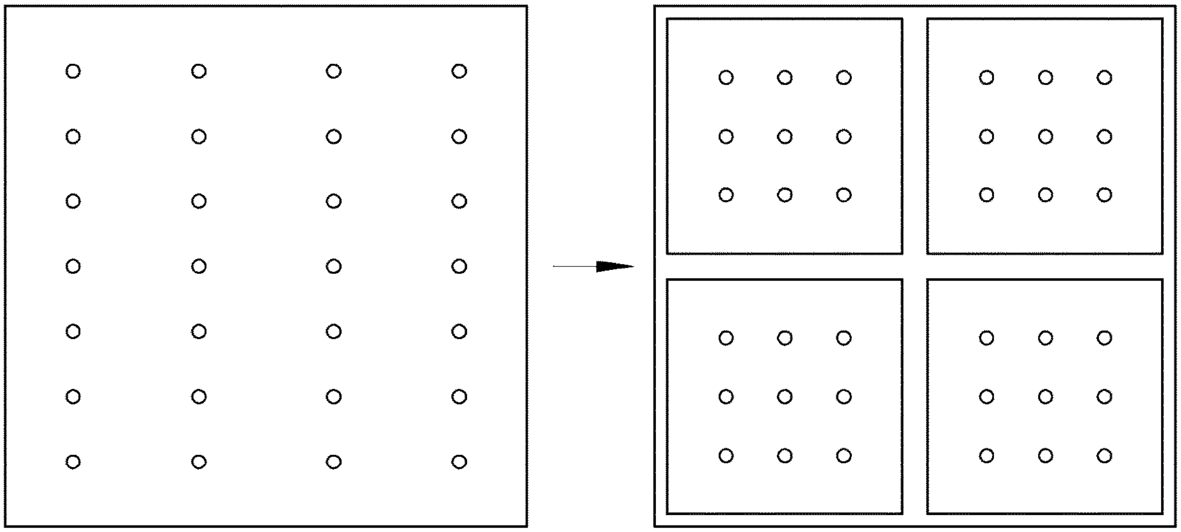
FIGS. 3 and 4 are schematic views illustrating a needle patch having N partitioned zones and N partitions according to an embodiment of the present invention.
Figure 4:
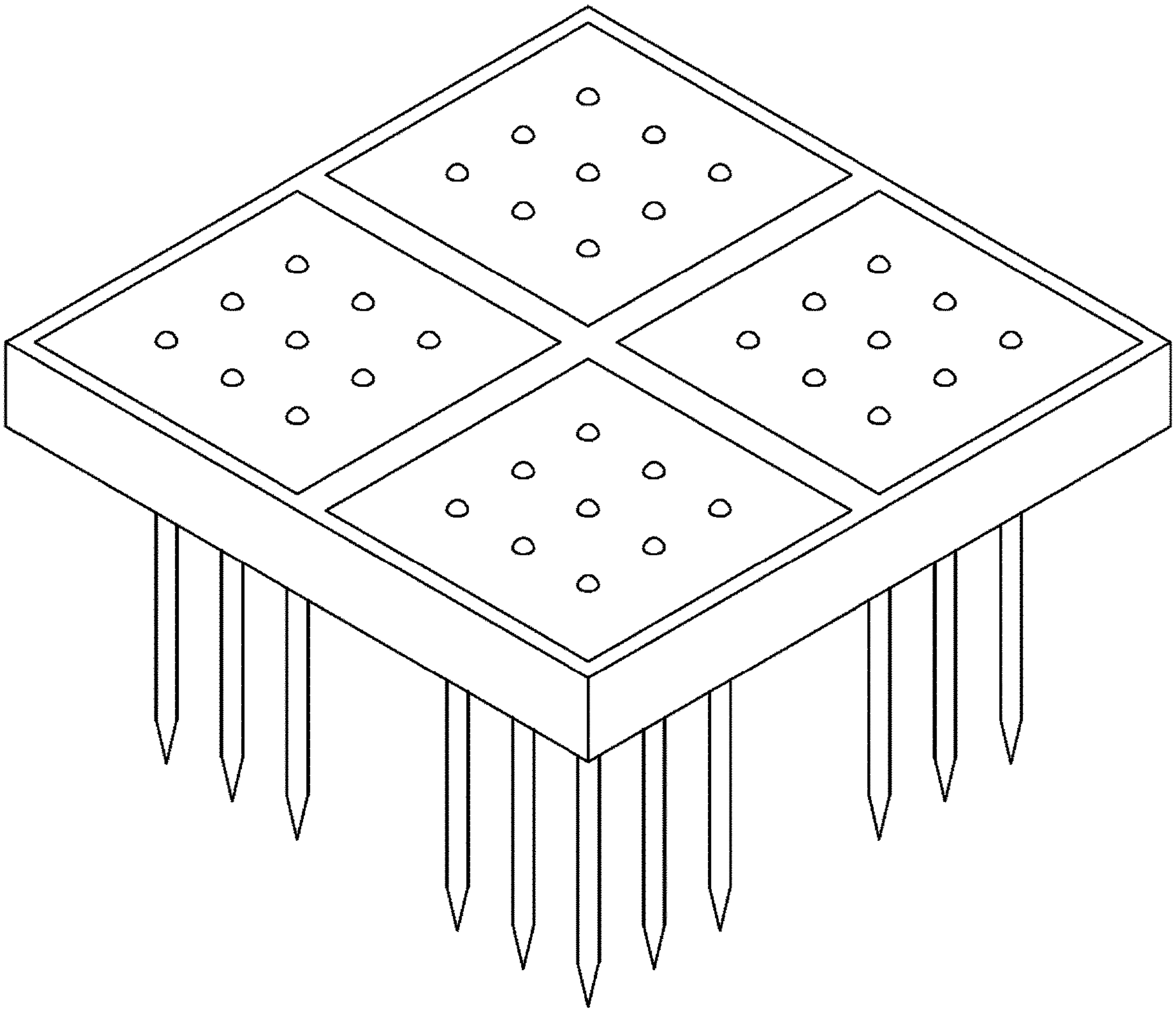
Figure 5:
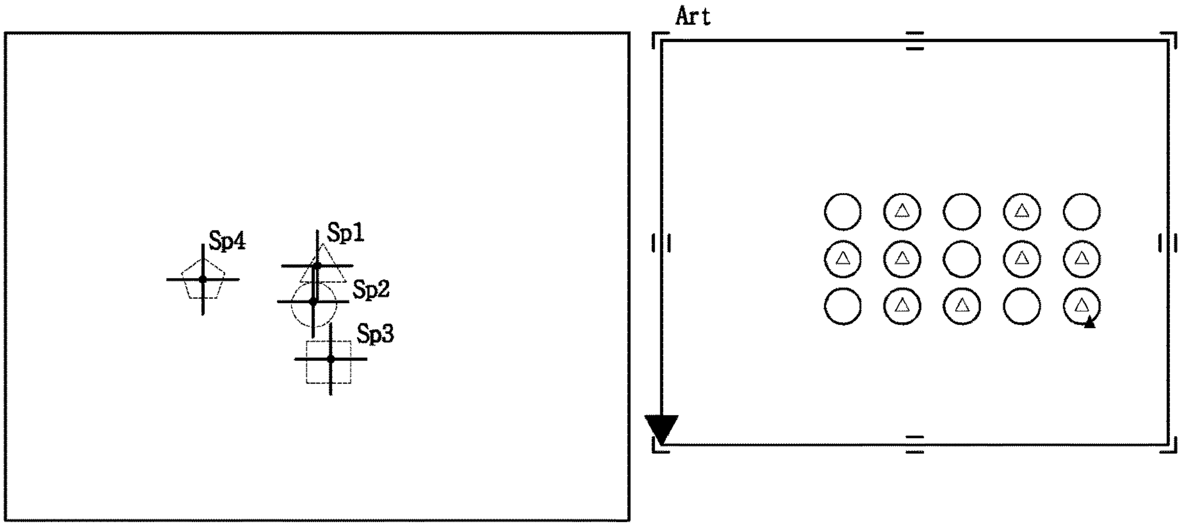
FIG. 5 is an experimental result image according to the present invention.

FIG. 3 and FIG. 4 are schematic views illustrating a needle patch having N partitioned zones and N partitions according to an embodiment of the present invention, and FIG. 5 is an experimental result image according to the present invention.

Referring to FIG. 5, an experiment in which heat is generated by high frequency in one needle in which a non-insulated zone is formed was conducted using animal tissue, and it can be seen that heat distribution is uneven when Step1 to Step3 and Step4 are compared. However, looking at an experiment in which heat is generated by high frequency in a plurality of needles in which non-insulated zones are formed in the present invention, the experiment shows that the heat is uniformly distributed. In addition, by using animal tissue, a phenomenon in which current is concentrated at edges of arrayed needles and causes protein denaturation only in the corresponding part (local part) is shown. That is, in the present invention, damage to the epidermal layer caused by a microneedle to which high frequency is applied may be minimized, energy may be uniformly distributed to partitioned zones of each patch according to the purpose of treatment so that a certain region of the skin and a local site may be effectively treated, and safety may be increased since the degree of skin damage is reduced due to the uniform energy distribution.

Although the exemplary embodiments of the present invention have been described hereinabove, those skilled in the art or those of ordinary skill in the art will understand that the present invention may be variously modified and changed within the scope not departing from the spirit and technical scope of the present invention described in the claims to be described later.

INDUSTRIAL APPLICABILITY

There are various acne scars including minor scars such as acne red marks and acne pigmentation scars that are relatively less visible and can be treated with little disruption to daily life, and severe scars such as pitted scars and hypertrophic scars that take a longer time to treat and require more downtime. In particular, the pitted scars may be classified into ice pick scars having an awl shape, boxcar scars having a box shape, and rolling scars with a rounded recessed shape according to their shape.

Pitted scar treatment began with laser peeling, which was previously treated by peeling off the skin, and took a leap forward with the launch of a laser treatment device called "Fraxel" in the United States in 2004. Currently, skin beauty devices for cosmetic purposes in addition to acne scar treatment have been commercialized. A fractional laser includes a laser having a wavelength such as 1410 nm, 1440 nm, 1540 nm, or 1550 nm which does not cause epidermal damage and a $CO_2$ fractional laser and an Er:YAG fractional laser having a wavelength that may peel off the skin, according to wavelength.

The invention claimed is:

1. A method for manufacturing a fractional microneedle module having partitioned zones using high frequency, the method comprising:

generating a flat plate made of a conductive material;

partitioning the flat plate having conductivity into m×m parts to generate N partitioned zones;

generating M grooves into which fractional microneedles are inserted in the N partitioned zones and inserting M fractional microneedles into the M grooves;

connecting each of the M fractional microneedles with an electrical connection terminal so that a high-frequency signal is applied to the M fractional microneedles; and uniformly distributing high-frequency energy to each of the N partitioned zones so that the high-frequency energy is uniformly injected into a dermal layer of skin due to the M fractional microneedles being electrically connected to the electrical connection terminal.

2. The method for claim 1, further comprising lowering a degree of skin damage and increasing safety by distributing energy of 1/N of input power to each of the N partitioned zones when the high-frequency signal is applied to the M fractional microneedles.

3. The method for claim 2, comprising arranging an interval between the M fractional microneedles at a boundary between one zone of the N partitioned zones, in which the energy of 1/N of the input power is distributed, and a zone adjacent to the one zone, such that a generated electric field of each zone is not affected.

4. The method for claim 1, further comprising:

providing an insulating film coated with an insulating material on a remaining portion of an outer circumferential surface of a body of each of the M fractional microneedles except for a conductive portion; and providing the insulating film as a parylene or Teflon material.

5. A method for manufacturing a fractional microneedle module having partitioned zones using high frequency, the method comprising:

generating a flat plate made of a conductive material;

partitioning the flat plate having conductivity into m×m parts to generate N partitioned zones;

generating M grooves into which fractional microneedles are inserted in the N partitioned zones and inserting M fractional microneedles into the M grooves;

connecting electrically isolated switching elements serving as switches in parallel for each of the N partitioned zones so that current is conducted sequentially or non-sequentially between the N partitioned zones;

allowing a high-frequency signal to be applied to each of the M fractional microneedles connected to an electrical connection terminal as the electrically isolated switching element is turned on; and injecting the high-frequency signal with an energy intensity of 1/N of input power to each of the N partitioned zones due to the M fractional microneedles being electrically connected to the electrical connection terminal.

6. The method for claim 5, wherein the electrically isolated switching element serves as an on/off switch, and only performs a role of turning on or off by inputting light as a signal to a gate (G) of the electrically isolated switching element.

7. The method for claim 6, comprising:

connecting X field effect transistor (FET) elements in parallel to form the electrically isolated switching element and allowing the electrically isolated switching element to serve as one switch; and distributing in parallel an amount of power input to the electrically isolated switching element due to a configuration of connecting the X FET elements in parallel.

8. The method for claim 5, further comprising controlling the switches in adjacent zones to switch in a same pattern as the N partitioned zones to prevent a phenomenon of instantaneous high voltage from appearing due to ripple noise generated at a boundary between one zone of the N partitioned zones and a zone adjacent to the one zone when the electrically isolated switching element is switched from off to on.

9. The method for claim 8, further comprising applying the input power only to a portion of the N partitioned zones to which the high-frequency signal is input by allowing the high frequency input signal to be transmitted to a gate of each of the N electrically isolated switching elements and non-sequentially switching each of the N electrically isolated switching elements to be turned on or off.

10. The method for claim 8, further comprising sequentially applying the input power to the N partitioned zones by allowing a same input signal as the high frequency signal to be transmitted to a gate of each of the N electrically isolated switching elements and sequentially switching each of the N electrically isolated switching elements to be turned on or off.

11. The method for claim 8, further comprising providing a switch control module allowing a same input signal as the high frequency signal to be transmitted to a gate of each of the N electrically isolated switching elements and configured to control the electrically isolated switching elements to be sequentially or non-sequentially switched.

* * * * *